United States Patent
Pursley

[11] Patent Number: 6,030,371
[45] Date of Patent: Feb. 29, 2000

[54] CATHETERS AND METHOD FOR NONEXTRUSION MANUFACTURING OF CATHETERS

[76] Inventor: Matt D. Pursley, 430 Cameron Woods Ct., Alpharetta, Ga. 30202

[21] Appl. No.: 08/918,713

[22] Filed: Aug. 22, 1997

Related U.S. Application Data

[60] Provisional application No. 60/024,344, Aug. 23, 1996.

[51] Int. Cl.[7] .......................... B05D 1/06; A61M 25/092; A61M 25/095; A61M 25/16
[52] U.S. Cl. ...................... 604/282; 427/2.12; 427/2.28; 427/2.3; 427/195; 427/202; 427/289; 427/358; 427/484; 427/485; 427/421; 427/422; 427/554; 600/114; 600/146; 604/264; 604/280; 604/283
[58] Field of Search ..................................... 427/2.3, 2.12, 427/2.25, 195, 289, 293, 554, 422, 425, 426, 461, 477, 482, 485, 2.28, 421, 202, 350; 604/264, 265, 280, 282; 600/114, 134, 139, 140, 144, 146, 153; 607/122; 118/56, 621, 630, 631, 400, 244

[56] References Cited

U.S. PATENT DOCUMENTS

| | | |
|---|---|---|
| 1,802,120 | 4/1931 | Maynard . |
| 3,009,209 | 11/1961 | Weinbrener . |
| 3,019,014 | 1/1962 | Miksis . |
| 3,736,202 | 5/1973 | Sorenson . |
| 3,749,621 | 7/1973 | Shoffner . |
| 3,800,798 | 4/1974 | Winkler ................. 128/349 R |
| 4,025,664 | 5/1977 | Gerek et al. ............... 427/183 |
| 4,026,747 | 5/1977 | DeLorean et al. .......... 156/171 |
| 4,281,674 | 8/1981 | Tanaka et al. .............. 134/95 |
| 4,385,635 | 5/1983 | Ruiz ......................... 128/658 |
| 4,434,126 | 2/1984 | McGary, Jr. et al. ..... 264/303 |
| 4,577,543 | 3/1986 | Wilson ......................... 87/11 |
| 4,616,064 | 10/1986 | Zukosky et al. ............ 525/92 |
| 4,636,346 | 1/1987 | Gold et al. ................ 264/139 |
| 4,686,124 | 8/1987 | Onohara et al. ............ 428/35 |
| 4,705,511 | 11/1987 | Kocak ...................... 604/167 |
| 4,722,344 | 2/1988 | Cambron et al. ......... 128/658 |
| 4,764,324 | 8/1988 | Burnham ................. 264/103 |
| 4,817,613 | 4/1989 | Jaraczewski et al. .... 128/658 |
| 4,835,022 | 5/1989 | Hühne ....................... 427/423 |
| 5,003,918 | 4/1991 | Olson et al. .............. 118/665 |
| 5,037,404 | 8/1991 | Gold et al. ................ 604/282 |
| 5,057,092 | 10/1991 | Webster, Jr. .............. 604/282 |
| 5,085,649 | 2/1992 | Flynn ....................... 604/280 |
| 5,116,652 | 5/1992 | Alzner ...................... 428/36.9 |
| 5,127,975 | 7/1992 | Zackrisson et al. ...... 156/171 |
| 5,135,599 | 8/1992 | Martin et al. ............ 156/294 |
| 5,178,902 | 1/1993 | Wong et al. .............. 427/470 |

(List continued on next page.)

*Primary Examiner*—Diana Dudash
*Attorney, Agent, or Firm*—Jeffrey L. Thompson; Thompson & Thompson, P.A.

[57] ABSTRACT

An apparatus and method for nonextrusion manufacturing of catheters that can be used to produce catheters having a simple or complex configuration. A polymer material in a particulate preform is applied in a layer over an outer surface of a core member. By applying the polymer material in a particulate preform, a composition of the polymer material can be varied continuously as it is being applied to provide a variable hardness over the length of the catheter. A fibrous reinforcement can be used having a constant or variable pitch and a constant or variable number of fibers and fiber types. Sensors can be easily placed in a wall of the catheter as the catheter is being fabricated, thereby allowing more sensors to be used without placing conductors in the lumen of the catheter. Deflection passages can be provided in a wall of the catheter for inserting a wire to deflect the catheter. The polymer material can be heated into molten form as it is being applied, or the core mandrel or liner can be heated to cause the polymer material to consolidate upon impact. A mandrel in the preferred embodiment is rotated about its longitudinal axis while a spray head and filament winding head traverse the length of the mandrel and apply polymer material and filament, respectively. Other arrangements can also be used, including a spray head and filament winding head that rotate about a continuous core mandrel, and a fluidized bed or other container into which a heated core mandrel is immersed. A plurality of mandrels can be placed side-by-side to form a multiple lumen tubing.

35 Claims, 11 Drawing Sheets

U.S. PATENT DOCUMENTS

| | | | |
|---|---|---|---|
| 5,250,059 | 10/1993 | Andreas et al. | 606/159 |
| 5,290,230 | 3/1994 | Ainsworth et al. | 604/96 |
| 5,318,032 | 6/1994 | Lonsbury et al. | 128/658 |
| 5,334,169 | 8/1994 | Brown et al. | 604/282 |
| 5,454,881 | 10/1995 | Fischer | 427/2.3 |
| 5,516,560 | 5/1996 | Harayama et al. | 427/245 |
| 5,537,729 | 7/1996 | Kolobow | 264/310 |
| 5,542,924 | 8/1996 | Snoke et al. | 604/95 |
| 5,558,659 | 9/1996 | Henke | 604/280 |
| 5,749,837 | 5/1998 | Palermo et al. | 600/585 |

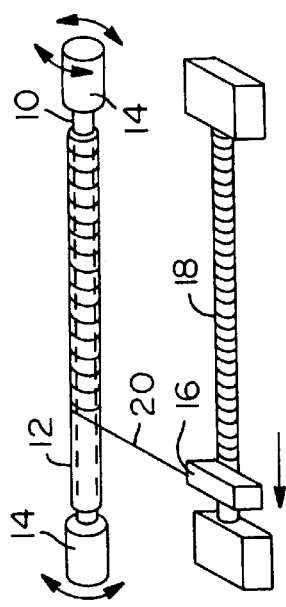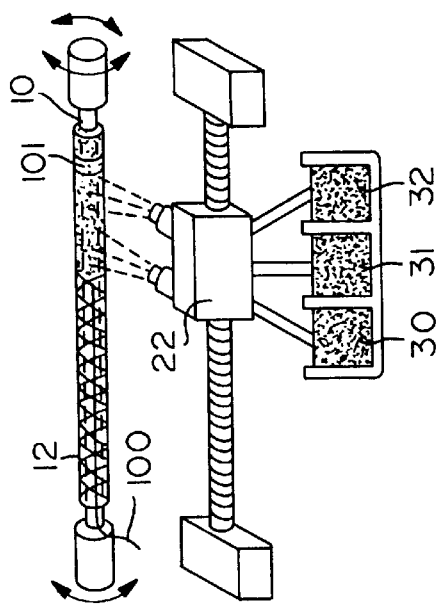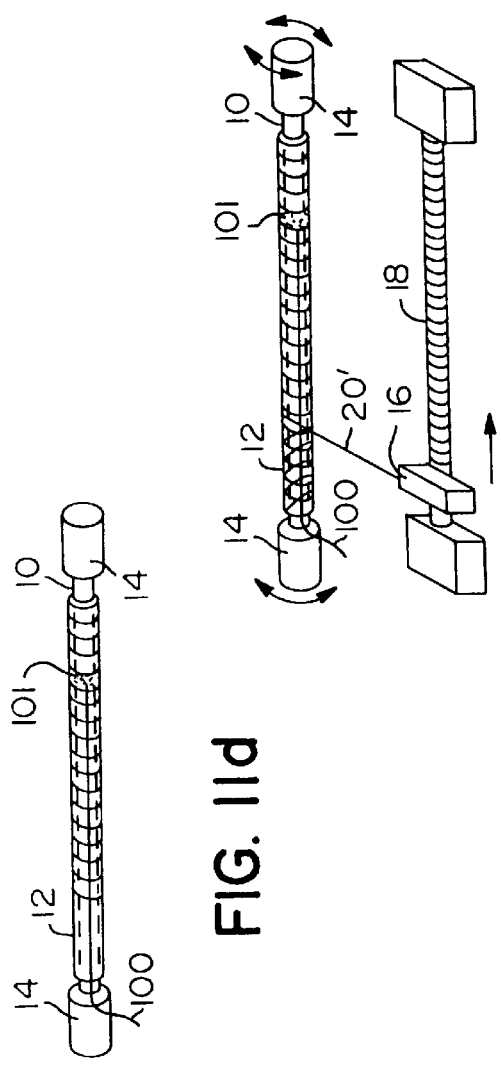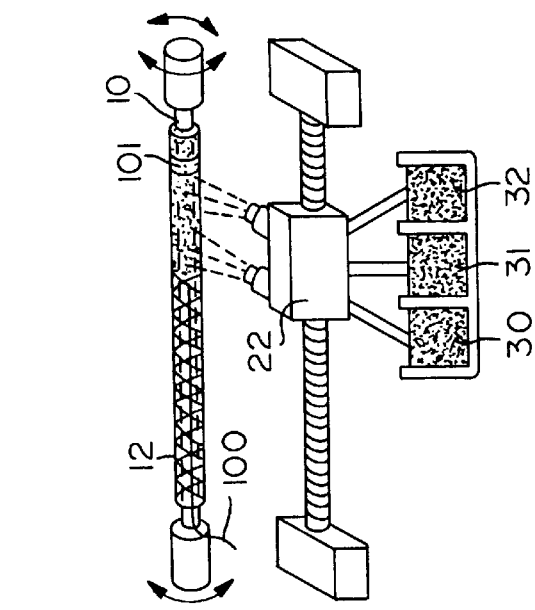

CATHETERS AND METHOD FOR NONEXTRUSION MANUFACTURING OF CATHETERS

This application claims priority from provisional U.S. Application Ser. No. 60/024,344, filed Aug. 23, 1996.

BACKGROUND OF THE INVENTION

1. Field of the Invention

The present invention relates generally to an apparatus and method for manufacturing tubing and, more particularly, to an apparatus and method for manufacturing catheters having a simple or complex configuration by applying a nonextruded layer of polymer material over a core member.

2. Description of the Related Art

Medical tubing and catheters are widely employed for a variety of treatment and diagnostic procedures involving, for example, the administration of fluid medications and devices into a patient and the removal of fluids from the patient. In this application, the terms "catheter" and "medical tubing" will be used interchangeably to refer to the same structure.

The ultimate use for which medical tubing is designed requires that the tubing have certain physical characteristics. For example, a catheter must be sufficiently stiff or rigid to enable its insertion and movement through narrow body orifices and channels and, in some applications, must also be able to withstand a high bursting pressure. On the other hand, a catheter must be sufficiently soft and flexible so that it may readily conform to body shapes so as not to cause injury to the interior wall of a patient's vessel as it is advanced. In addition, a catheter must be of sufficient mechanical strength to resist tearing during normal use, such as when the catheter is removed against tissue resistance.

Catheters have been manufactured for several years by numerous methods. Mechanical performance requirements of catheters have increased over time because of new procedures, such as angioplasty and therapeutic and diagnostic neurological procedures. In these applications, it is desirable to have a catheter that varies in hardness along its shaft length. Conventional methods to meet this requirement consist of segmenting the wall of the catheter with plastics having varying hardness. The segments are generally individual tubes bonded together, or segments of varying hardness within a laminated-type construction. The transition from hard to soft polymer in these types of constructions is abrupt and may require many segments to achieve the desired hardness transition, which complicates manufacture.

Other methods for manufacturing catheters having varying hardness along the length of the catheter have been disclosed. For example, U.S. Pat. No. 4,385,635 (RUIZ) and U.S. Pat. No. 5,085,649 (FLYNN) each discloses a catheter tubing having tapered resin layers of different hardness. The tapered layers are formed by a controlled extrusion process using, for example, a bi-orifice extrusion head with a controlled discharge rate to keep the combined thickness of the respective layers constant. Because these methods rely on an extrusion process to form the tapered layers, they are relatively expensive to implement and are difficult to control in a manner that achieves an optimum hardness transition over the length of the catheter. The tapered layers also tend to make it difficult to incorporate reinforcement filament into the catheter during manufacturing.

Catheters are often employed for diagnostic procedures that require sensors to be placed within body orifices. An example of one such catheter 200 is shown in FIGS. 15 and 16. In this conventional catheter, a tubing 201 is first formed using a conventional extrusion process or the like. A hole 202 is then formed in the wall 203 of the tubing 201. A conductor wire 204 is then inserted through the lumen of the tubing 201 and out through the hole 202 (or vice versa). A surface electrode 205 in the form of a metal band is electrically connected to the conductor wire 204 and placed over the hole 202 around the outer surface of the catheter 200. The surface electrode 204 functions as a sensor.

This conventional sensor arrangement for catheters has a number of disadvantages. The conductor wire 204 is placed within the lumen of the catheter 200, thereby interfering with the passage of fluids and the like through the lumen. The process of assembling the conductor wire 204 and surface electrode 205 to the catheter 200 is quite difficult since the catheter 200 is formed separately from the sensor and conductor wire.

Nylon powders are commercially available for use as painting or chrome alternatives to eliminate harmful emissions and waste products during metal plating operations, for example. These nylon powders have been applied using electrostatic/baking applications that produce films over metal substrates and the like having a thickness in the range of 0.004 to 0.050 inches. In conventional applications of the powders, the substrate is grounded, the plastic powder is charged and applied with a spray or fluidized bed exposure, and then the powder-coated substrate is baked. This known technology has not previously been adopted in a catheter manufacturing process.

SUMMARY OF THE INVENTION

An object of the present invention is to solve the problems associated with the prior art catheter manufacturing methods described above.

More specifically, an object of the present invention is to provide a cost effective process and apparatus for manufacturing catheters having a simple or complex configuration.

It is a further object of the present invention to provide a process and apparatus for manufacturing catheters having a continuous change in hardness over the length of the catheter.

It is a further object of the present invention to provide a process and apparatus for manufacturing catheters using a polymer material in a particulate preform without using an extrusion process.

It is a further object of the present invention to provide a process and apparatus for manufacturing catheters which permits great flexibility in the composition of the catheter walls, the size and number of lumen, the placement of opacifier markers, the hardness over the length of the catheter, and the placement of fibrous reinforcement, conductors, sensors, and deflection passages in the catheter walls.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

The present invention provides an apparatus and method for manufacturing catheters that produces an improved catheter, having a simple or complex configuration, by applying a nonextruded layer of polymer material in a particulate preform over a length of a core member. The polymer material can be provided in the form of a powder, such as thermoplastic or thermosets, or in the form of a solvenated polymer, such as urethanes, epoxies, polyimides, and so forth.

Since the polymer material is applied in a nonextrusion process, the composition of the polymer material can be varied continuously as it is being applied to thereby provide a variable hardness over the length of the catheter. A fibrous reinforcement can be used having a constant or variable pitch and a constant or variable number of fibers and fiber types. Sensors can be easily placed in a wall of the catheter as the catheter is being fabricated, thereby allowing more sensors to be used without placing conductors in the lumen of the catheter. Deflection passages can be provided in a wall of the catheter for inserting a wire to deflect the catheter. The core member can be a mandrel or a liner placed over a mandrel.

In the preferred embodiment, a mandrel is rotated about its longitudinal axis while a spray head and a filament winding head traverse the length of the mandrel and cover the mandrel with layers of polymer and filament, respectively. According to another embodiment, a continuous core mandrel is used, and a spray head and filament winding head are mounted for rotation around the continuous core mandrel. According to yet another embodiment, a heated core member is immersed in a fluidized bed or other suitable container to apply the polymer coating over the core member. A plurality of mandrels can be placed side-by-side to form a multiple lumen tubing. A conventional or laser sizing arrangement is used to provide final sizing of the catheter without contacting the catheter mechanically.

The polymer material can be consolidated onto the core substrate by heating the polymer material into a molten state before applying it to the core substrate, or by heating the core substrate and applying the polymer material in powder form. In the latter method, the polymer material is melted and consolidated over the surface of the core substrate as it impacts on the core substrate.

More specifically, a first aspect of the present invention comprises a method of making medical tubing, comprising the steps of providing a core having an outer surface, providing a polymer material in a particulate preform, and applying a nonextruded layer of the polymer material in its particulate preform over a length of the outer surface of the core. The method may further comprise the step of varying a composition of the polymer material while the layer of polymer material is being applied to thereby provide the layer of polymer material with a variable hardness over at least a portion of a length of the core.

A liner may be placed over a core mandrel before applying the layer of polymer material, wherein the liner functions as the core. The invention can also be practiced by applying the layer of polymer material directly to the core mandrel. The composition of the polymer material can be varied by mixing two or more polymer materials each having a different hardness, and changing a ratio of the first polymer material to the second polymer material as the layer of polymer material is applied. An opacifier material can also be selectively mixed with the polymer materials and applied in a uniform layer over the catheter or in the form of opacifier rings selectively spaced along the length of the catheter. Several other variations and details of the method according to this aspect of the present invention are described in the detailed description provided below.

A second aspect of the present invention comprises an apparatus for manufacturing medical tubing, comprising a core having an outer surface, a supply of polymer material in a particulate preform, and means for applying a nonextruded layer of the polymer material in its particulate preform over a length of the outer surface of the core. The apparatus may also have a means for varying a composition of the polymer material while the layer of polymer material is being applied to thereby provide a variable hardness over at least a portion of a length of the tubing. Several variations and details of the apparatus according to this aspect of the present invention are described below.

A third aspect of the present invention comprises an improved catheter comprising a nonextruded layer of polymer material having a continuously changing hardness over at least a portion of a length of the catheter. The catheter may comprise a liner over which the layer of polymer material is placed. The layer of polymer material preferably has a uniform thickness over a length of the catheter, and a reinforcement filament embedded within the layer of polymer material. Opacifier marks may be selectively spaced over the length of the catheter.

The layer of polymer material in the catheter can comprise different color shades corresponding to different ratios of polymers used in the layer of polymer material, thereby providing a visual indication of a hardness transition. The catheter comprises either a single lumen or multiple lumens extending therethrough. In one variation, a conductor and sensor can be embedded in the layer of polymer material. In another variation, a longitudinal deflection passage can be formed in the layer of polymer material with a resilient fiber extending through the passage and anchored adjacent a distal end of the passage, whereby the catheter can be deflected by applying a force to a proximal end of the resilient fiber. Other variations and details of the improved catheter according to this aspect of the present invention are described below.

BRIEF DESCRIPTION OF THE DRAWINGS

Preferred embodiments of the present invention will be described in detail hereinafter with reference to the accompanying drawings. In the drawings:

FIGS. 11*a*, 11*b*, 11*c*, 11*d*, 11*e* and 11*f* show a series of process steps for manufacturing a catheter having a conductor wire and a sensor embedded in a wall of the catheter.

DETAILED DESCRIPTION OF THE INVENTION

Preferred embodiments of the invention will now be described in detail with reference to FIGS. 1 to 14 of the drawings.

Figure 1A:
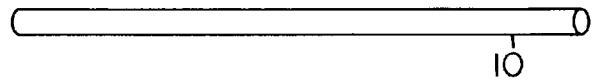
FIGS. 1a, 1b, 1c and 1d show a series of process steps for manufacturing a catheter according the present invention.

The basic method of manufacture according to a first embodiment of the present invention will be described below by making reference to FIGS. 1*a* to 1*d*. According to the method, a core mandrel 10 is first selected, as shown in FIG. 1*a*, over which the catheter will be constructed.

Figure 1B:
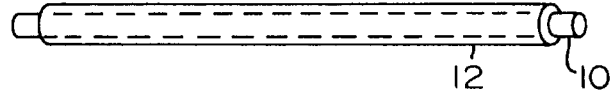

A catheter liner 12 is then placed over the mandrel 10, as shown in FIG. 1*b*. The liner 12 can be formed of a variety of different materials but is generally less than 20% of the intended wall thickness. As an example, a liner having a 0.00150 inch wall thickness of TFE can be used. Alternatively, the process of the present invention can be performed without a liner, whereby a polymer coating is applied directly over the mandrel 10.

Figure 1C:
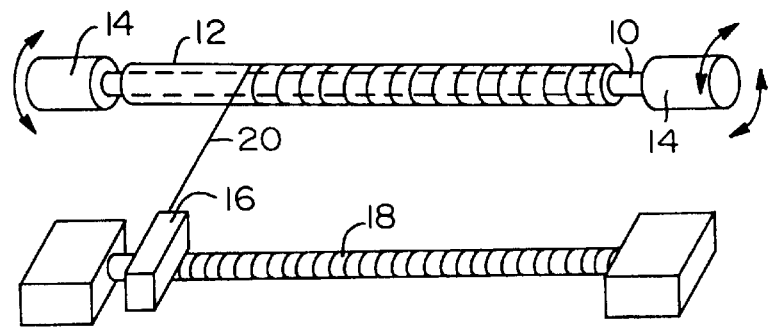
Figure 1D:
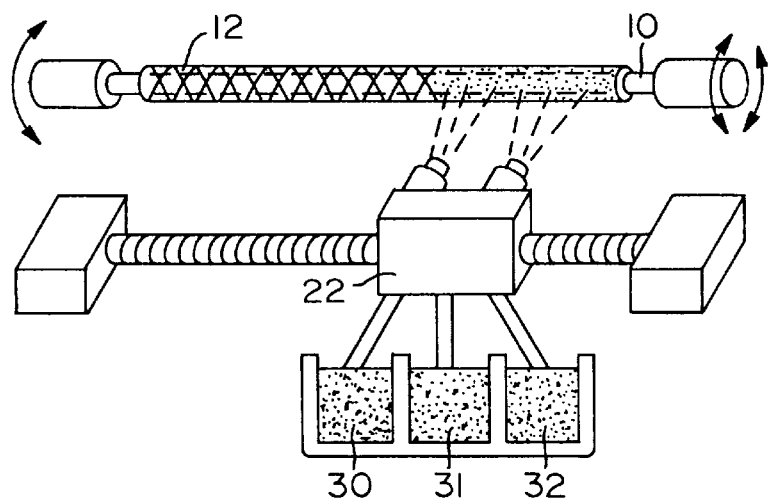

A combination of reinforcement filament and polymer material is then applied over the liner 12, as shown in FIGS. 1*c* and 1*d*. During this operation, the mandrel/liner combination is loaded into rotating chucks 14. A filament winding head 16 is then traversed on a screw carrier 18 longitudinally along the mandrel 10 to apply fibrous reinforcement filament 20 over the mandrel at a winding angle range of 0 to 90 degrees relative to the longitudinal axis of the catheter (this is a far superior range than achieved in current braiding/wrapping operations). For portions of the catheter that require great circumferential rigidity or kink resistance, a very tight winding angle (e.g., 80 to 90 degrees) of the reinforcement filament 20 can be used, and for portions of the catheter that require low rigidity, the reinforcement filament 20 can be applied in a low winding angle (e.g., 0 to 10 degrees). The winding angle of the reinforcement fiber 20 can be continuously varied over the length of the catheter by controlling the rotation speed of the mandrel 10 and the movement of the filament winding head 16 along the support 18.

Figure 2:
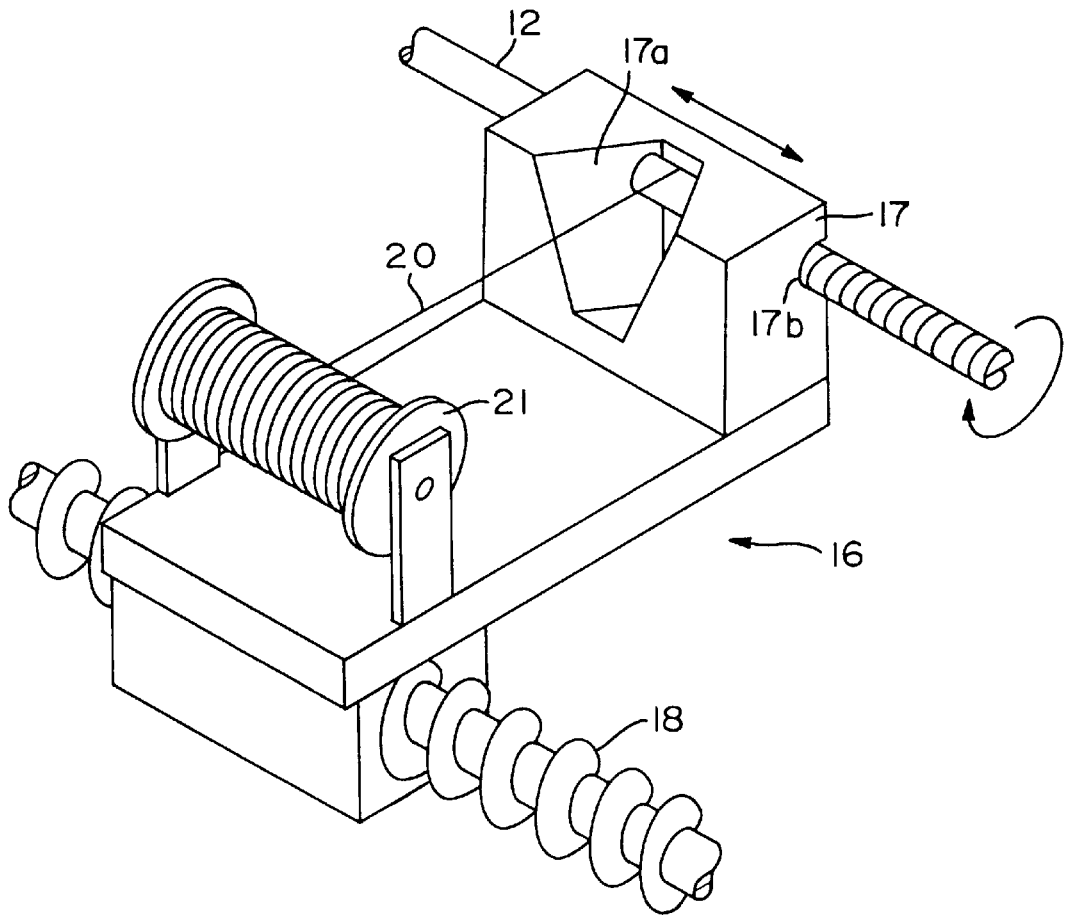
FIG. 2 is a perspective detail view showing a winding head used in the present invention.

A detail of the winding head 16 is shown in FIG. 2. As seen in FIG. 2, the winding head 16 is constructed so that the mandrel/liner is supported by a grooved member 17 during winding to keep the mandrel 10 from bending due to the tension in the reinforcement fiber 20. The grooved member 17 includes an opening 17*a* through which the fiber 20 is passed from a spool 21 of the winding head 16 to the liner 12. A groove 17*b* is formed in the member 17 on both sides of the opening 17*a* for receiving and supporting the mandrel/liner.

At either the same time, or after winding, an atomizing spray head 22 also traverses the mandrel/liner, as shown in FIG. 1*d*. The spray head 22 applies an atomized spray (e.g., a molten polymer in an inert gas stream) that thermally fuses to the substrate it impinges upon (i.e., the mandrel 10, the liner 12, or the reinforcement fiber 20). The substrate can be preheated to ensure complete fusion of the sprayed polymer to the substrate. This preheating can be accomplished with infrared, hot air, or resistance heating of the core mandrel 10 or other suitable means.

Figure 3:
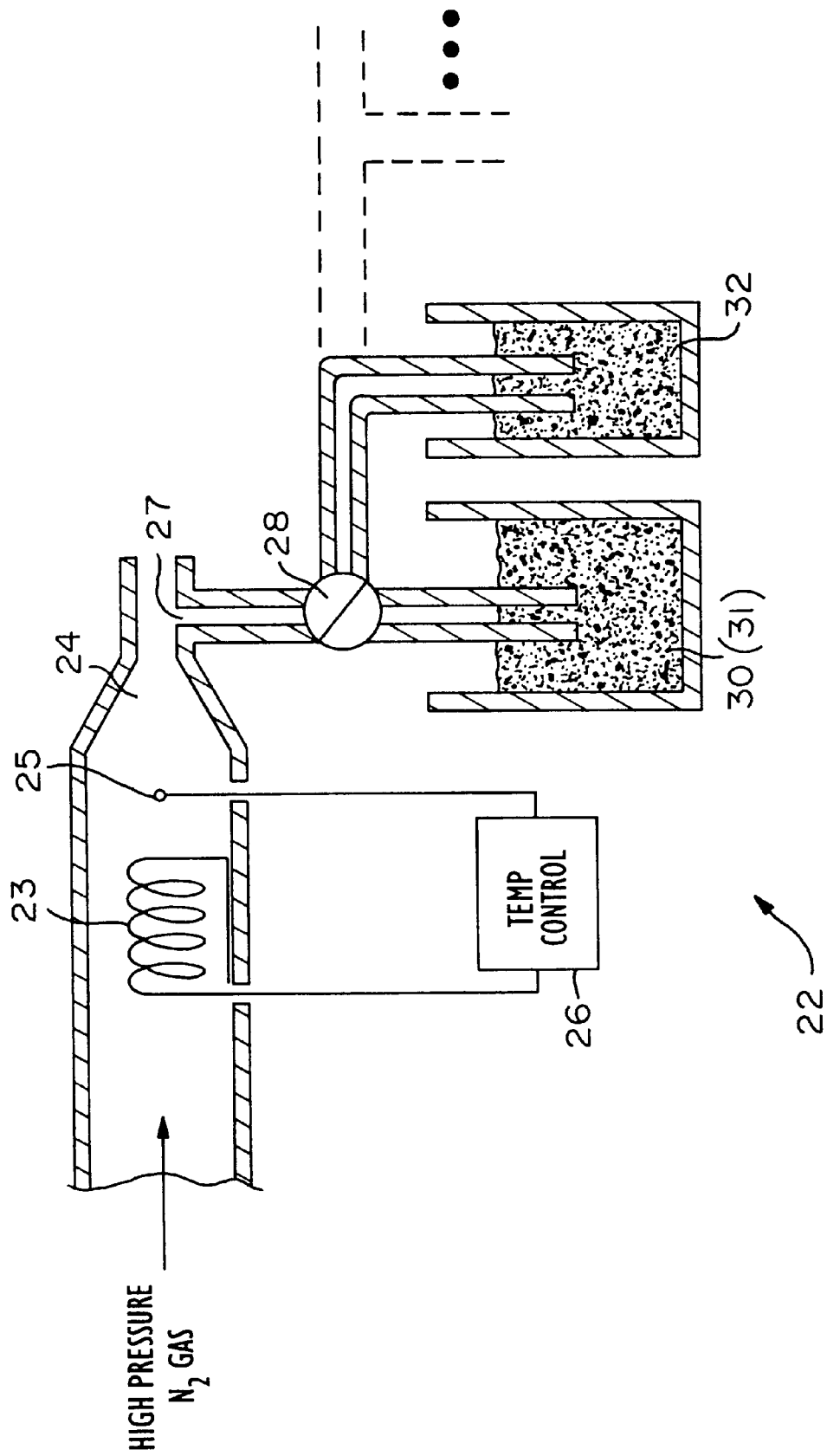
FIG. 3 is a sectional view of an atomizing spray head for applying a molten material to a catheter liner according to a first embodiment of the present invention.

The atomized spray head 22 according to a first embodiment of the present invention is shown in detail in FIG. 3. As shown, high pressure gas, such as nitrogen, is piped past a heater 23 and through a venturi 24 of the spray head 22. A temperature sensor 25, such as a thermocouple, is provided in the flow within the spray head 22 to monitor the gas temperature. A temperature controller 26 is used to maintain the desired temperature of the gas flowing through the venturi 24.

The throat 27 of the venturi 24 is connected to a digitally controlled metering valve 28, which in turn is connected to multiple containers 30, 31 of plastic powders or the like having varying hardness and also to a container 32 of opacifying powder such as tungsten.

While the mandrel/liner is spinning, the atomizing spray head 22 traverses along a path parallel to the axis of the rotating mandrel/liner. As it traverses this path, the metering valve 28 is set such that only the harder polymer (e.g., from the container 30) is applied at what will be the proximal end of the catheter. As the head 22 traverses the mandrel/liner, the metering valve 28 is controlled such that it ports to the harder polymer to a lesser degree and to the softer polymer (e.g., from the container 31) to a higher degree until finally only the softest polymer is applied at the distal tip of the catheter, which will serve as the soft tip of the catheter-body.

Figure 4:
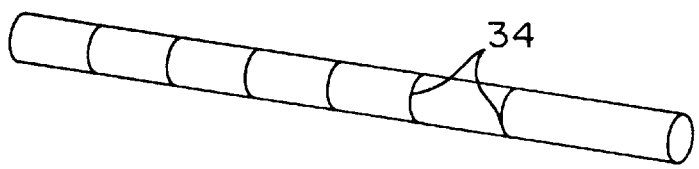
FIG. 4 is a perspective view of a catheter manufactured by the present invention having evenly spaced opacifier marks.

In a similar fashion, opacifying powder can be selectively applied from the container 32. A single layer of polymer can be applied as the filaments are placed. The single layer of polymer can be followed by a layer of opacifier and finally a finish layer of polymer. A significant benefit of applying opacifier in this manner is that the movement of the head 22 can be paused momentarily to apply circumferential rings 34 of high opacifier concentration, as shown in FIG. 4. The circumferential rings 34 serve as markers on the catheter when the catheter is used under X-ray. The opacifier powder in this embodiment can be heated to a high enough temperature so that it melts the substrate it impinges upon and thereby adheres to the surface of the substrate until it is overcoated with a finish layer of polymer.

After the catheter is completely coated with polymer from the spray head 22, the catheter is rough-sized by passing a cutter over the surface of the catheter and then polished. The catheter body is then removed from the rotating chucks 14 and is ready for finishing operations, such as curving or hubbing.

Figure 5:
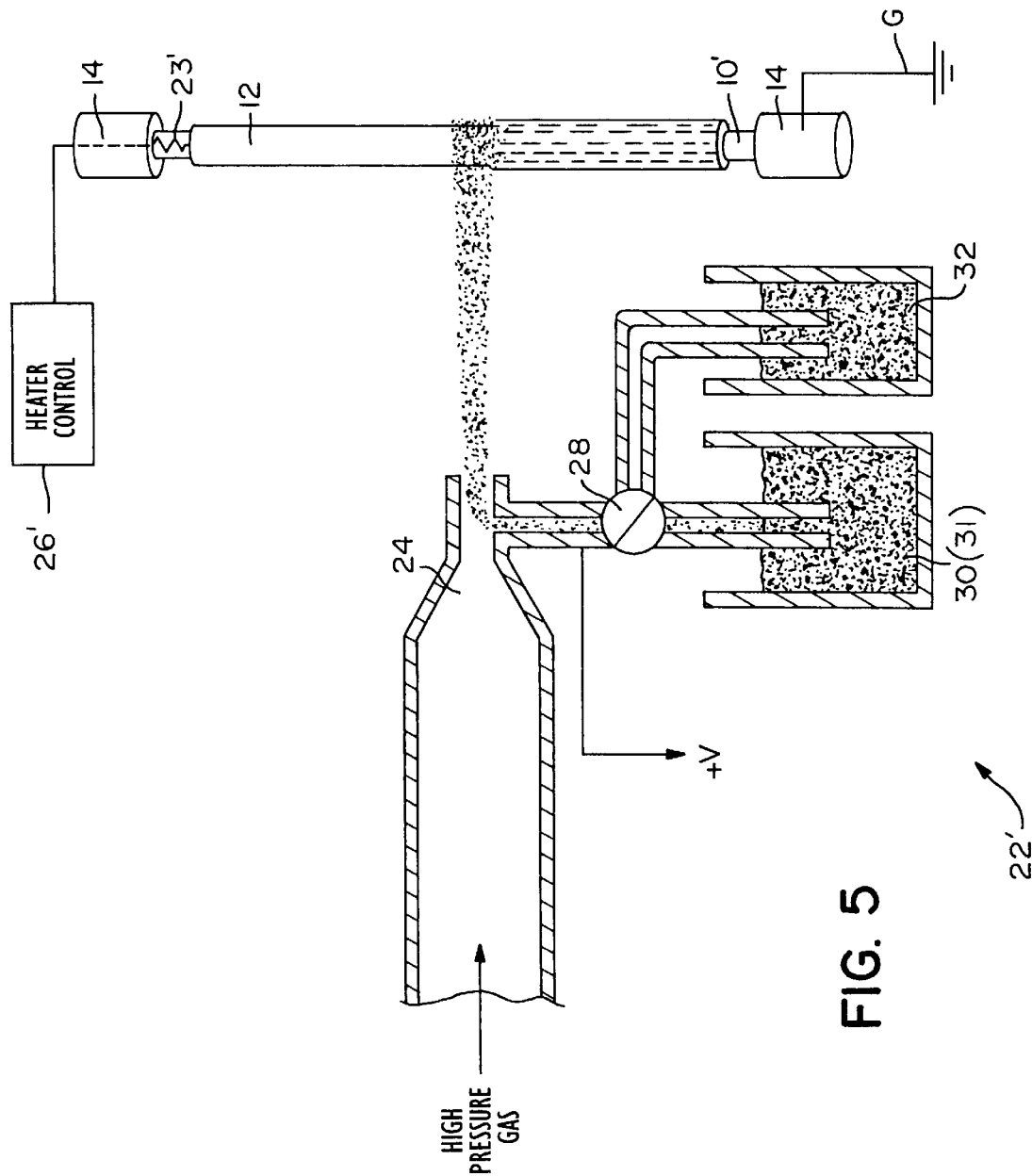
FIG. 5 is a sectional view of an arrangement for applying a powder material to a heated mandrel/liner according to a second embodiment of the present invention.

A second embodiment of the invention will next be described by making reference to FIG. 5 of the drawings. As shown in FIG. 5, the catheter manufacturing method according to the present invention is performed by applying an unmelted polymer powder to a heated mandrel/liner.

In this embodiment, the mandrel 10' and liner 12 are heated by a heater 23' to above the melting point of the powder material (e.g., above 380 degrees F for plastic powder). The heater 23' can be a resistance heater controlled by a heater controller 26', as shown in FIG. 5. Alternatively, the heater can be an infrared or hot air heater, or other suitable means for heating the mandrel 10' or liner 12 to the required temperature for melting the powder material.

The unmelted powder is then sprayed onto the surface of the heated mandrel 10' or liner 12 using the spray head 22'. The metering valve 28 operates as described above to selectively dispense powder materials from containers 30, 31 and 32 to form a catheter having a continuously variable hardness and opacifier content. As shown in FIG. 5, the mandrel 10' is preferably grounded through a ground G, and the powder material is charged through a positive source +V as the unmelted powder is applied, thereby causing the powder to electrostatically cling to the heated mandrel 10' or liner 12 during application. When the powder impinges upon the heated mandrel 10' or liner 12, the powder melts to form a uniform coating over the surface thereof. A series of fine coating layers can be applied over the mandrel 10' or liner 12 by making several passes of the spray head 22' over the length or selected portions of the catheter. The coated mandrel or liner can then be baked to further consolidate and cure the coating as necessary.

Figure 6:
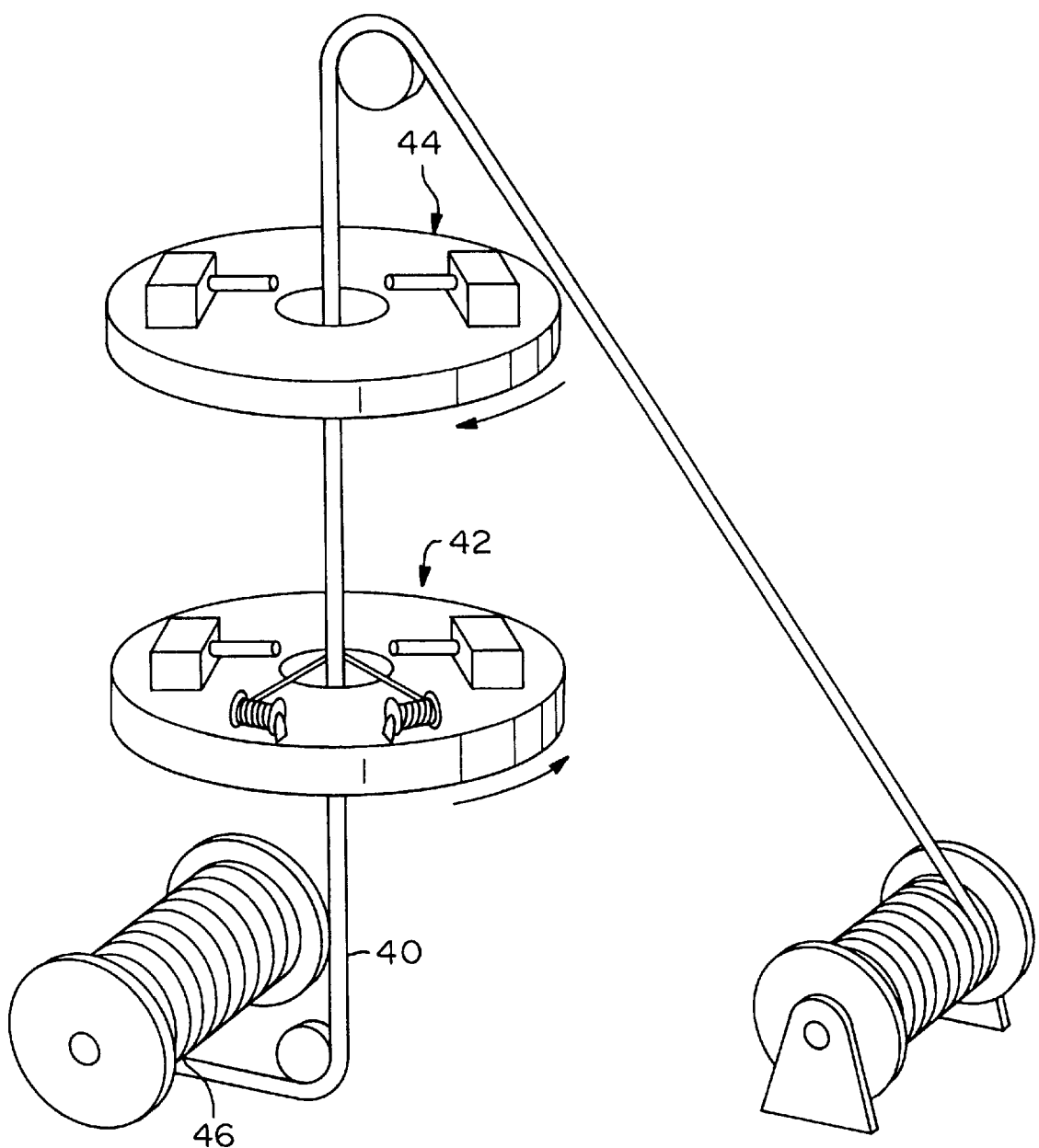
FIG. 6 is a perspective view of a third embodiment of the present invention wherein a series of rotating fiber and spray heads are used to manufacture catheters using a continuous core mandrel.

FIG. 6 shows a third embodiment wherein the process according to the present invention is used to form a continuous length of tubing by feeding a continuous core mandrel 40 through a series of rotating tables 42, 44. Each rotating table 42, 44 is provided with one or more filament winding and spray heads similar to those described above.

Figure 7A:
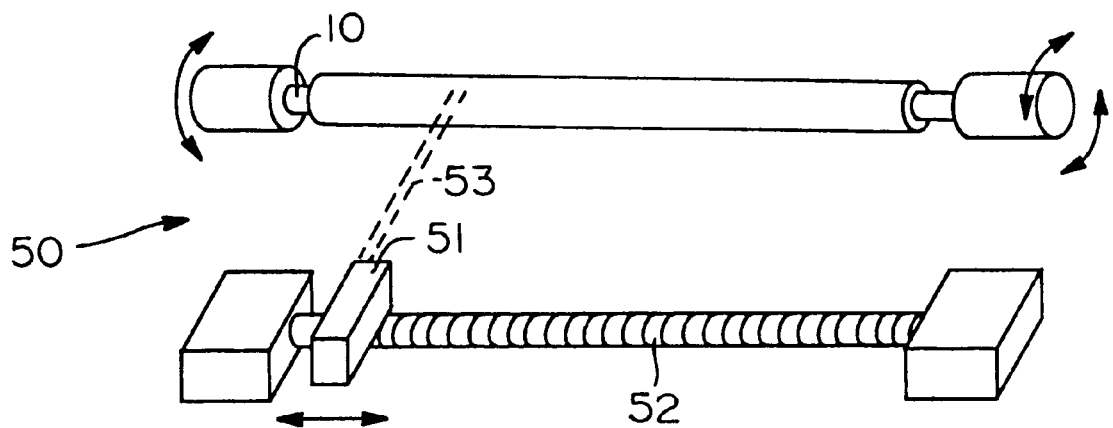
FIGS. 7a and 7b show a laser arrangement in perspective and sectional views, respectively, for sizing the tubing without mechanical contact after the polymer coating is consolidated over the mandrel.
Figure 7B:
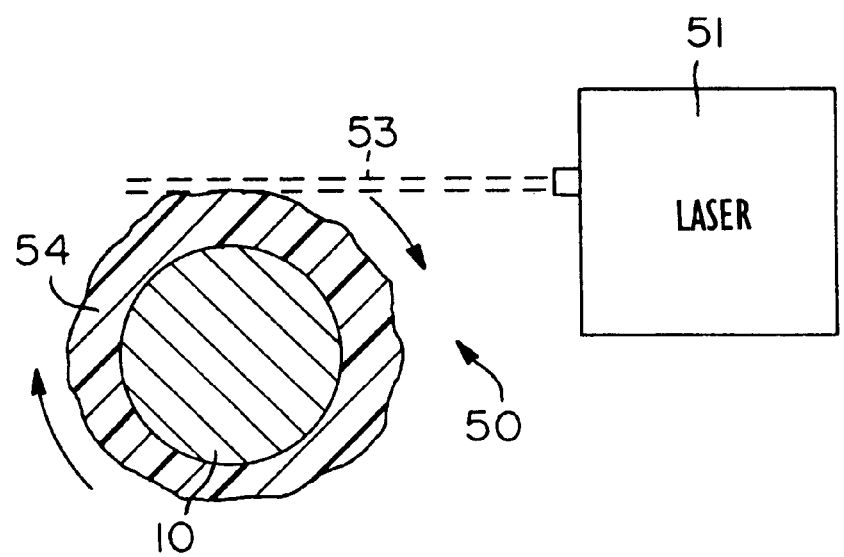

FIGS. 7a and 7b show a laser arrangement 50 for sizing the tubing after the polymer coating is consolidated on the liner/mandrel. As shown, the laser arrangement 50 includes a laser cutter 51 which can be moved along a threaded shaft 52 or the like for movement parallel to the rotating mandrel 10. The laser cutter 51 emits a laser beam 53 (e.g., an ultraviolet laser beam) which is directed to impinge on a tangential surface of the polymer coating 54. The laser beam 53 provides a means for sizing the tubing using laser energy without mechanically contacting the tubing. By eliminating mechanical contact with the rotating tubing, the tubing can be sized with greater precision and without the inherent defects caused by deflections in the mandrel during mechanical cutting and grinding operations. The laser cutter 51 can also be controlled to taper the catheter over its length.

Figure 8A:
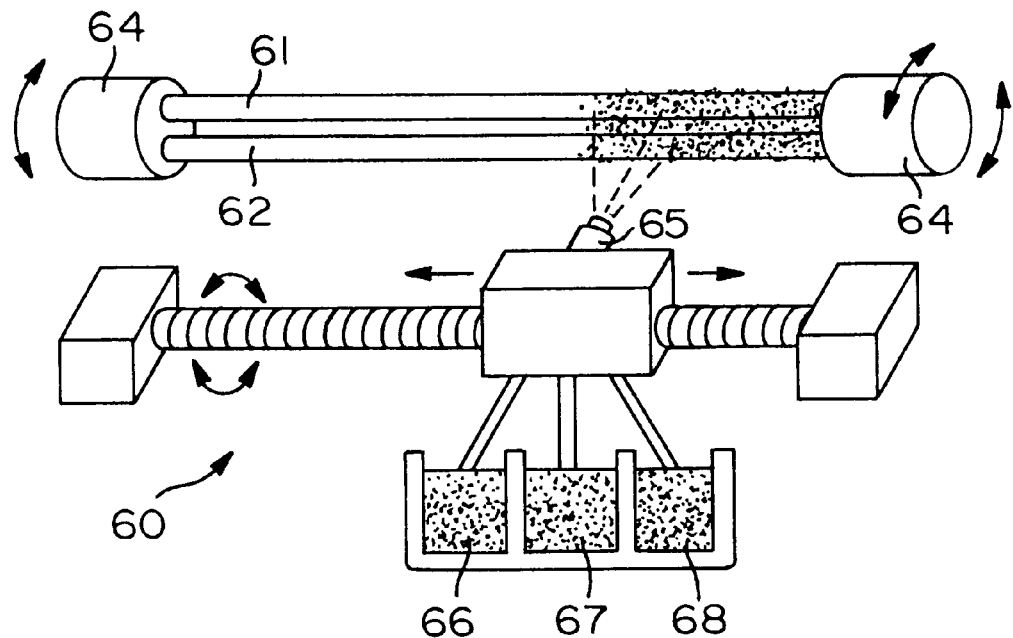
FIGS. 8a and 8b show a fourth embodiment of the present invention which is used to manufacture medical tubing having multiple lumens.
Figure 8B:
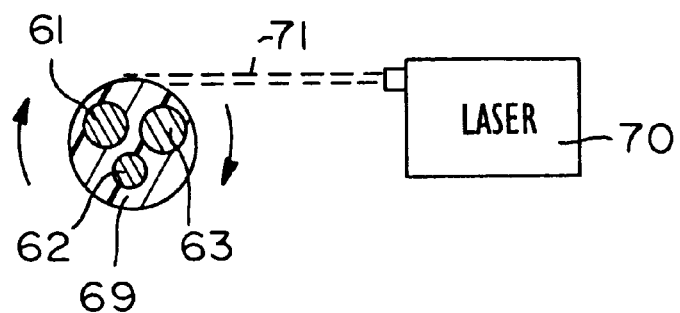

FIGS. 8a and 8b show an apparatus 60 according to a fourth embodiment of the present invention for manufacturing medical tubing having multiple lumens. As shown in FIG. 8a, a plurality of mandrels 61, 62 are loaded side-by-side into rotating chucks 64 and extend parallel to each other. A spray head 65 or other application means is then used to apply a selected mix of polymer powders and opacifiers from containers 66, 67, and 68 to the mandrels 61, 62, each of which can be heated to consolidate the powder upon impact. Each of the mandrels 61, 62 defines a lumen through the multiple lumen catheter formed by the process.

FIG. 8b shows a laser arrangement for sizing the multiple lumen tubing after the polymer coating 69 is consolidated on the mandrels 61, 62, 63. As shown, the laser arrangement includes a laser cutter 70 that emits a laser beam 71 which is directed to impinge on a tangential surface of the polymer coating 69. The laser arrangement shown in FIG. 8b is similar to the laser arrangement shown in FIGS. 7a and 7b.

Figure 9:
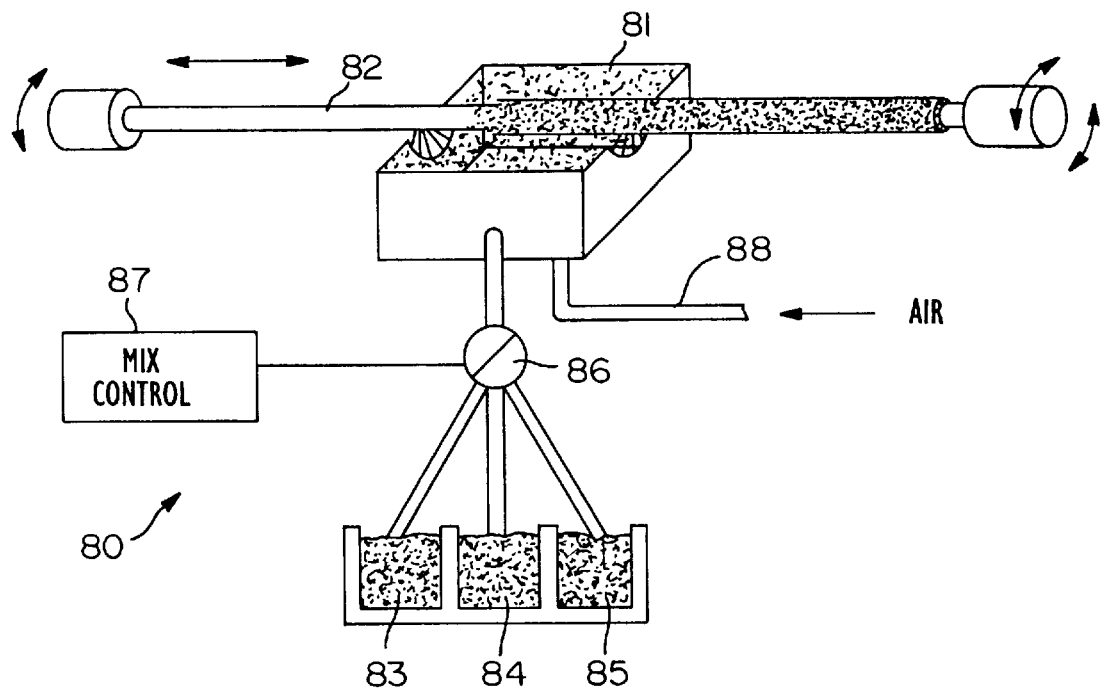
FIG. 9 shows a fifth embodiment of the present invention wherein a fluidized bed is used to apply a polymer coating to the mandrel.

FIG. 9 shows an apparatus 80 according to a fifth embodiment of the present invention wherein a fluidized bed 81 is used to apply a polymer coating over a mandrel 82. The fluidized bed 81 receives a selected ratio of polymers and opacifiers from a plurality of containers 83, 84, 85. A digitally controlled valve 86 or the like is controlled by a mix controller 87 to port to the different containers 83, 84, 85 to adjust the mixture in the fluidized bed 81. The fluidized bed 81 is connected through a conduit 88 to a source of air or other suitable fluid which is blown through several openings in a bottom surface of the bed 81 to create a "boiling froth" of the mixture in the bed 81. The mandrel 82 is heated and rotated as it passes through the fluidized bed 81 to cause the polymer mixture in the fluidized bed 81 to consolidate and cling to the mandrel 82 to form a uniform layer. As in the other embodiments, a plurality of polymer layers having a selected hardness can be applied over the mandrel 82 using the fluidized bed 81 to create a catheter having an optimized hardness at each portion along its length.

Figure 10:
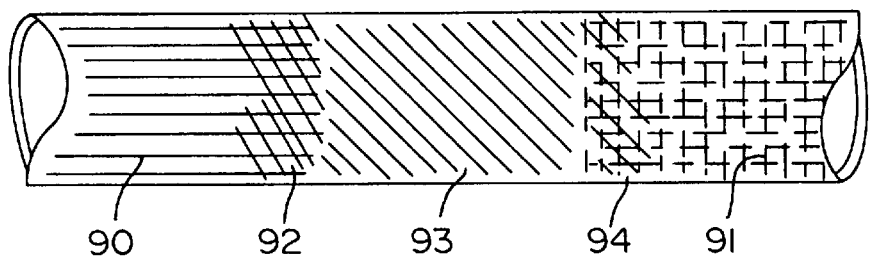
FIG. 10 shows a catheter having different color shades indicating the transition in hardness over the length of the catheter.

The different hardness polymers used in the manufacturing process according to the present invention can be colored to provide visual confirmation of the transition of hardness, as shown in FIG. 10. For example, the "hard" polymer in the container 30 can be blue and the "soft" polymer in the container 31 can be yellow, thereby causing the most rigid portion 90 of the catheter to be blue, the softest portion 91 of the catheter to be yellow, and the intermediate portions 92, 93, 94 of the catheter to be different shades of green depending on the relative proportions of each polymer applied.

The present invention is particularly useful for manufacturing catheters having a conductor wire and sensor formed therein. A series of process steps for manufacturing such a catheter are shown in FIGS. 11a through 11f. The first three process steps, as shown in FIGS. 11a, 11b, and 11c, correspond to the first three process steps shown in FIGS. 1a, 1b, and 1c, as described above. In these first process steps, a catheter liner or first layer of polymer material 12 is placed over the core mandrel 10 (FIG. 11b), and then covered by a first layer of reinforcement filament 20 (FIG. 11c).

A conductor wire 100 and sensor 101 are then placed on top of the first layer of reinforcement filament 20, as shown in FIG. 11d. A second layer of reinforcement filament 20' is then wound over the conductor wire 100 (FIG. 11e), thereby securing the conductor wire 100 and sensor 101 in a selected position. As described above, the winding angle of the reinforcement fibers 20, 20' can be continuously varied over the length of the catheter by controlling the rotation speed of the mandrel 10 and the movement of the filament winding head 16 along the support 18. A final coating of polymer material is then applied using the spray head 22 in the manner described above (FIG. 11f).

Figure 12:
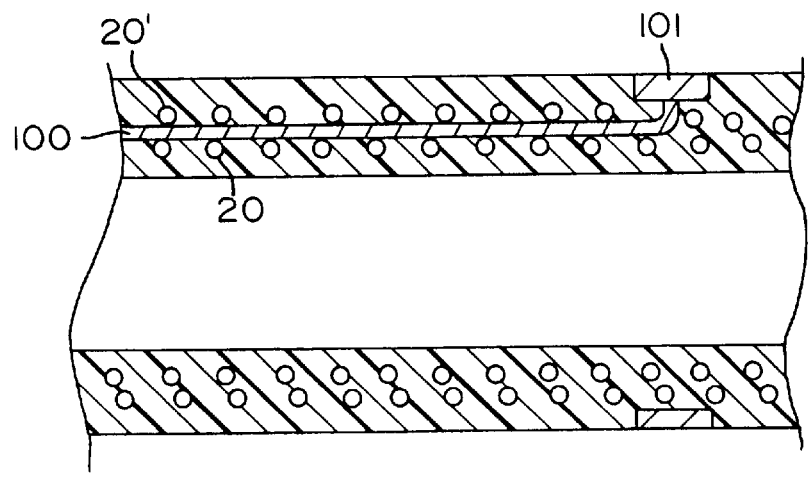
FIG. 12 is a cross-sectional view of a catheter according to the present invention wherein a conductor wire and sensor are embedded in a wall of the catheter.
Figure 13:
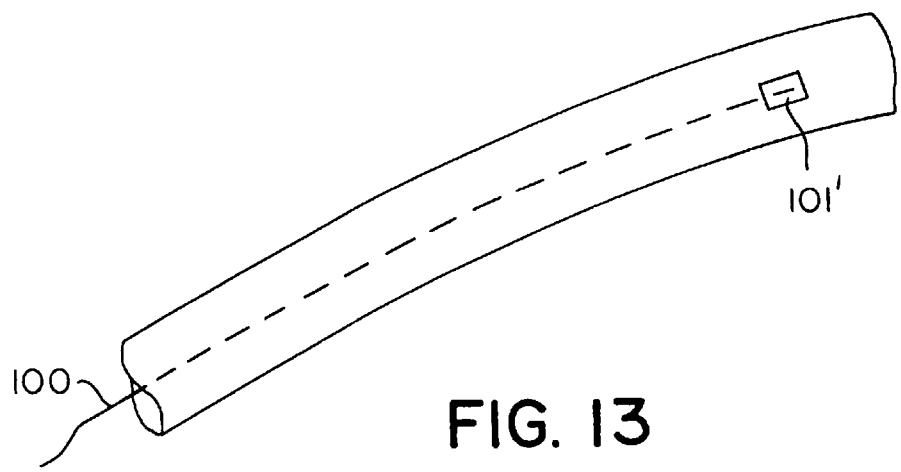
FIG. 13 is a perspective view of a catheter having a single point sensor and conductor wire embedded in a wall of the catheter.

The conductor wire 100 is thus embedded in the wall of the catheter while the wall is being formed, thereby eliminating the difficult assembly process required by the conventional catheter and sensor assembly. As shown in FIG. 12, the conductor wire 100 is sandwiched between the two layers of reinforcement fibers 20, 20', and the sensor 101 is positioned flush with the outer surface of the catheter. Alternatively, a single point sensor 101', rather than a band-shaped sensor, can be placed in the wall of the catheter, as shown in FIG. 13. Such a single point sensor was not possible with the conventional catheter assembly.

The sensors 101, 101' placed in the wall of the catheter according to the present invention can be in the form of pressure transducers, surface electrodes, capacitive electrodes/plates, temperature sensors, strain gauges, and so forth.

Figure 14:
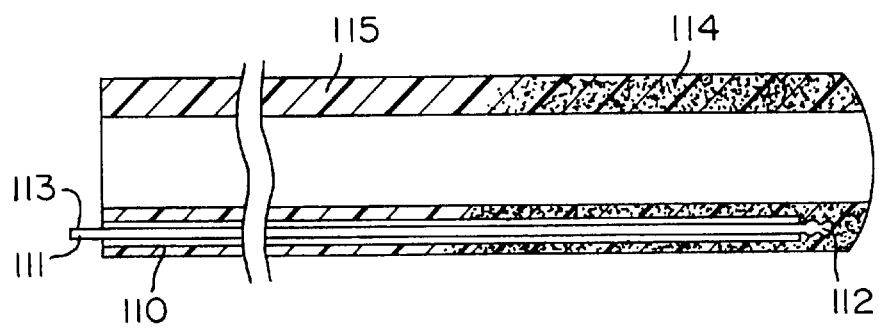
FIG. 14 is a cross-sectional view of a catheter according to the present invention wherein a deflection passage and resilient fiber are embedded in a wall of the catheter for deflecting the catheter.
Figure 15:
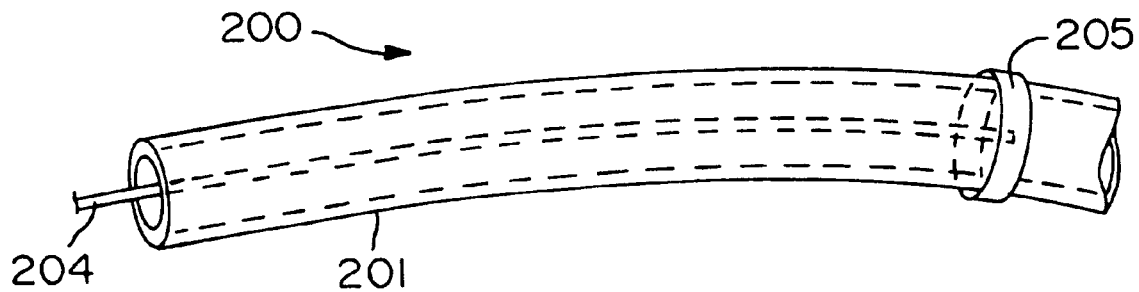
FIG. 15 is a perspective view of a conventional catheter and sensor assembly.
Figure 16:
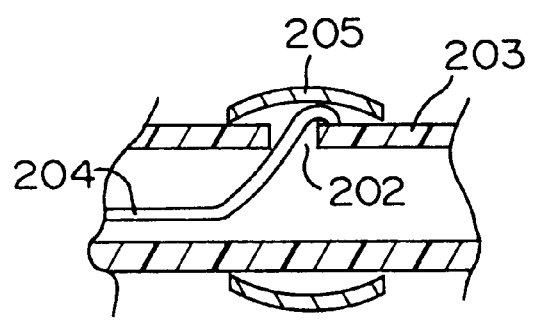
FIG. 16 is a cross-sectional view of the conventional catheter and sensor assembly shown in FIG. 15.

FIG. 14 is a cross-sectional view of a catheter according to the present invention wherein a longitudinally extending passage is formed in a wall of the catheter by embedding a polyimide tube 110 or the like in the wall as the catheter is formed by the process described above. A resilient fiber, such as a spring temper wire 111, is inserted through the lumen of the tube 110 and has a distal end 112 embedded and anchored in a distal end of the catheter wall. The wire 111 is sized such that it would be freely slideable in the tube 110 if the wire 111 was not anchored at its distal end 112.

The catheter can be deflected or bent by applying a pushing or pulling force to a proximal end 113 of the wire 111. The catheter wall is preferably formed with a varying hardness along its length, whereby a soft portion 114 of the wall is at the distal end of the catheter, and a hard portion 115 of the wall is at the proximal end of the catheter. When a pulling force is applied to the proximal end 113 of the wire 111, the soft portion 114 of the catheter will deflect to "steer" the distal end of the catheter in a controlled manner.

A suitable polyimide tube for use as the tube 110 can have, for example, an inside diameter of 0.008 inch and an outside diameter of 0.009 inch. The wire 111 inserted through the tube 110 can be, for example, a spring temper wire having a 0.006 inch diameter.

It should be noted that, in certain applications, the reinforcement fibers can be omitted in any of the above-described embodiments. Also, as mentioned above, the process can be performed with or without a prefabricated liner placed over the mandrel. If a liner is not used, a thin layer of polymer can be applied over the metal surface of the mandrel using the spray head or other application means according to the present invention. The thin layer of polymer can then function as a liner over which the reinforcement fiber can be wound.

The present invention is not limited to only those processes described above for applying polymer powder to the mandrel. For example, in a rather crude arrangement according to the invention the mandrel can be heated and dipped into one or more containers containing the desired ratios of polymer powders. In this case, the heated mandrel will cause the powder to consolidate and cling to the mandrel as it is dipped into each container. The shearing action of the melt/powder interface will provide excellent "wet out" (solid-liquid-solid curing) of high viscosity polymers. The length of time of immersion can be used to control the buildup or thickness of the polymer material on the mandrel. The polymer powder can also be applied to the heated mandrel using a spatula or the like. The consolidated powder can then be sized and finished using a laser or other cutting means as described above.

The present invention provides a low cost method for manufacturing both simple and complex catheters. The disclosed method can be used to make a straight catheter tube that has no change in hardness and nothing embedded in the wall, or a complex catheter having any combination of the following features: (1) a variable hardness of plastic along a length of the catheter; (2) a fibrous reinforcement having a constant or variable pitch, a constant or variable number of fibers, and one or more different types of fibers; (3) sensors and conductor wires placed in the catheter wall as the wall is fabricated; (4) a deflection passage and wire embedded in the catheter wall for steering the catheter; and (5) multiple lumens having the same or different diameters.

It will be appreciated that the present invention is not limited to the exact construction that has been described above and illustrated in the accompanying drawings, and that various modifications and changes can be made without departing from the scope and spirit thereof. It is intended that the scope of the invention protected be limited only by the appended claims.

What is claimed is:

1. A method of making medical tubing, comprising the steps of:
   providing a core having an outer surface;
   providing first and second polymer materials, said first polymer material having a different hardness than said second polymer material;
   applying a nonextruded layer comprising a mixture of said first and second polymer materials over a length of said outer surface of the core by spraying said polymer materials toward the core such that particles of said polymer materials cover the outer surface of the core and are consolidated to form the medical tubing; and
   changing a mixed ratio of said first polymer material to said second polymer material as said polymer materials ate being sprayed toward the core to provide a continuous transition of hardness over a length of the tubing.

2. The method of making medical tubing according to claim 1, wherein said polymer materials are provided in powder form for applying to said core.

3. The method of making medical tubing according to claim 1, wherein said polymer materials are provided in a solution of solvent for applying to said core.

4. The method of making medical tubing according to claim 1, further comprising the step of placing a liner over a core mandrel before applying the layer of polymer material, said liner comprising said core.

5. The method of making medical tubing according to claim 1, further comprising the step of winding a filament about said core before applying the layer of polymer material.

6. The method of making medical tubing according to claim 1, further comprising the step of rotating the core while applying the layer of polymer material.

7. A method of making medical tubing, comprising the steps of:
   providing a core having an outer surface;
   providing at least one polymer material;
   applying a nonextruded layer of said polymer material over a length of said outer surface of the core such that particles of said polymer material impact on the outer surface of the core and are consolidated to form the medical tubing; and
   heating the polymer material into a molten state before the polymer material impacts on the outer surface of said core.

8. The method of making medical tubing according to claim 1, further comprising the steps of heating the core and spraying the polymer materials in powder form onto the heated core, wherein the polymer materials are consolidated on the core as a result of the heated core melting the polymer materials.

9. The method of making medical tubing according to claim 1, further comprising the step of selectively applying opacifier material to said core to form a plurality of opacifier rings along the length of the tubing.

10. The method of making medical tubing according to claim 1, further comprising the step of sizing the tubing by grinding or cutting an outer surface of the tubing after applying the layer of polymer material.

11. The method of making medical tubing according to claim 1, further comprising the step of sizing the tubing by passing a laser beam over a tangential surface of the layer of polymer material.

12. The method of making medical tubing according to claim 1, further comprising the step of providing a spray head to apply the layer of polymer material to the core, and rotating the spray head about the core while applying the polymer material.

13. A method of making medical tubing, comprising the steps of:

providing a core having an outer surface;

providing at least one polymer material;

applying a nonextruded layer of said polymer material over a length of said outer surface of the core such that particles of said polymer material are consolidated to form the medical tubing; and grounding the core and charging the polymer material to cause the polymer material to cling to the core electrostatically as the polymer material is applied.

14. A method of making medical tubing having multiple lumens; comprising the steps of:

providing a plurality of cores each having an outer surface;

placing said plurality of cores in close proximity to each other;

providing at least one polymer material; and applying a nonextruded layer of polymer material over a length of said outer surfaces of said plurality of cores such that particles of said polymer material are consolidated to form the medical tubing having multiple lumens.

15. A method of making medical tubing, comprising the steps of:

providing a core having an outer surface:

providing at least one polymer material;

applying a nonextruded layer of said polymer material over a length of said outer surface of the core such that particles of said polymer material are consolidated to form the medical tubing;

placing at least one conductor and at least one sensor over said nonextruded layer of polymer material; and applying a second nonextruded layer of polymer material over said conductor.

16. The method of making medical tubing according to claim 15, further comprising the steps of:

winding a first filament about said medical tubing before placing said conductor and said sensor;

winding a second filament about said medical tubing after placing said conductor and said sensor; and applying said second nonextruded layer of polymer material over said filaments and said conductor.

17. A method of making medical tubing, comprising the steps of:

providing a gore having an outer surface;

providing at least one polymer material;

applying a nonextruded layer of said polymer material over a length of said outer surface of the core such that particles of said polymer material are consolidated to form the medical tubing;

forming at least one longitudinal passage in said nonextruded layer of polymer material;

placing a resilient fiber into said longitudinal passage; and anchoring a distal end of said resilient fiber adjacent a distal end of said longitudinal passage, whereby the medical tubing can be deflected by applying a force to a proximal end of said resilient fiber.

18. A method of making a tubular structure, comprising the steps of:

applying a nonextruded layer of polymer material over a length of a core substrate; and varying a composition and color of said polymer material while said layer of polymer material is being applied to thereby provide said layer of polymer material with a variable hardness and color over at least a portion of a length of the core substrate, whereby a change in the hardness of the layer of polymer material is indicated by a change in color of the layer of polymer material.

19. The method of making a tubular structure according to claim 18, further comprising the steps of:

mixing a first polymer material with a second polymer material, said first polymer material having a different hardness than said second polymer material; and changing a mixed ratio of said first polymer material to said second polymer material as said layer of polymer material is applied to provide a variable hardness over a length of the tubular structure.

20. The method of making a tubular structure according to claim 19, further comprising the step of selectively mixing an opacifier material with the first and second polymer materials as said layer of polymer material is applied.

21. The method of making a tubular structure according to claim 18, further comprising the steps of:

providing at least first and second polymers having different hardnesses and different colors; and selectively mixing said first and second polymers to vary a hardness in the layer of polymer material, whereby a transition in the hardness of the layer of polymer material is indicated by a change in color of the layer of polymer material.

22. The method of making a tubular structure according to claim 18, further comprising the steps of:

forming at least one longitudinal passage in said nonextruded layer of polymer material;

placing a resilient fiber into said longitudinal passage; and anchoring a distal end of said resilient fiber adjacent a distal end of said longitudinal passage, whereby the tubular structure can be deflected by applying a force to a proximal end of said resilient fiber.

23. A catheter comprising a tubular structure manufactured by the method defined in claim 18.

24. A catheter comprising a nonextruded layer of polymer material having a continuously changing hardness over at least a portion of a length of the catheter, wherein said layer of polymer material comprises different color shades providing a visual indication of hardness.

25. The catheter according to claim 24, further comprising a liner, said layer of polymer material covering an outer surface of said liner.

26. The catheter according to claim 24, wherein said layer of polymer material has a uniform thickness over said portion of the catheter.

27. The catheter according to claim 24, further comprising a reinforcement filament embedded within said layer of polymer material.

28. The catheter according to claim 24, further comprising at least one opacifier mark extending about a circumference of the catheter.

29. The catheter according to claim 24, further comprising a plurality of opacifier marks spaced along the length of the catheter.

30. The catheter according to claim 24, further comprising multiple lumens extending through the catheter.

31. A catheter comprising a nonextruded layer of polymer material having a continuously changing hardness over at least a portion of a length of the catheter, further comprising at least one conductor and at least one sensor embedded in said layer of polymer material.

32. A catheter comprising a nonextruded layer of polymer material having a continuously changing hardness over at least a portion of a length of the catheter, further comprising at least one longitudinal passage embedded in said layer of polymer material and a resilient fiber extending through said longitudinal passage, a distal end of said resilient fiber being anchored adjacent a distal end of the longitudinal passage, whereby the catheter can be deflected by applying a force to a proximal end of said resilient fiber.

33. The method of making medical tubing according to claim 3, wherein said polymer material is consolidated by driving off the solvent.

34. The method of making medical tubing according to claim 10, wherein said step of sizing the tubing comprises grinding or cutting the tubing to have a tapering thickness over a length of the tubing.

35. The method of making medical tubing according to claim 11, wherein said step of sizing the tubing comprises using the laser beam to create a tapering thickness over a length of the tubing.

* * * * *